United States Patent
Bi

(10) Patent No.: US 8,434,355 B1
(45) Date of Patent: *May 7, 2013

(54) HIGH PRESSURE HIGH TEMPERATURE LINEAR SWELL METER

(76) Inventor: Hongfeng Bi, Houston, TX (US)

( * ) Notice: Subject to any disclaimer, the term of this patent is extended or adjusted under 35 U.S.C. 154(b) by 323 days.

This patent is subject to a terminal disclaimer.

(21) Appl. No.: 12/807,406

(22) Filed: Sep. 3, 2010

(51) Int. Cl.
*E21B 49/00* (2006.01)
*G01N 15/08* (2006.01)

(52) U.S. Cl.
USPC .............. 73/152.11; 73/152.05; 73/152.07; 73/37; 73/38

(58) Field of Classification Search ............... 73/37, 38, 73/152.11, 863, 865.6
See application file for complete search history.

(56) References Cited

U.S. PATENT DOCUMENTS

| | | | | |
|---|---|---|---|---|
| 2,445,494 A * | 7/1948 | Redmond | | 436/27 |
| 3,216,242 A | 11/1965 | Eyrich | | |
| 3,505,860 A * | 4/1970 | Bishop et al. | | 73/807 |
| 3,817,109 A * | 6/1974 | Audet et al. | | 73/865.6 |
| 3,877,312 A * | 4/1975 | Audet et al. | | 73/865.6 |
| 4,359,901 A * | 11/1982 | Bates et al. | | 73/152.11 |
| 4,649,737 A * | 3/1987 | Jones | | 73/38 |
| 4,982,604 A * | 1/1991 | Davis et al. | | 73/152.11 |
| 5,115,684 A * | 5/1992 | Haeussler | | 73/861.48 |
| 5,253,518 A | 10/1993 | Steiger et al. | | |
| 5,275,063 A * | 1/1994 | Steiger et al. | | 73/865.6 |
| 5,325,723 A * | 7/1994 | Meadows et al. | | 73/794 |
| 5,670,717 A * | 9/1997 | Lamine et al. | | 73/152.11 |
| 6,247,358 B1 * | 6/2001 | dos Santos | | 73/152.11 |
| 6,269,684 B1 * | 8/2001 | Maki et al. | | 73/53.01 |
| 7,143,653 B2 * | 12/2006 | Abdel-Hadi et al. | | 73/819 |
| 7,240,545 B1 * | 7/2007 | Jennings | | 73/149 |
| 7,472,588 B2 * | 1/2009 | Slavin et al. | | 73/152.11 |

* cited by examiner

*Primary Examiner* — Peter Macchiarolo
*Assistant Examiner* — Natalie Huls

(57) ABSTRACT

A method and apparatus for monitoring swelling changes consists of a cylindrical cell assembly (80) capable of withstanding high pressure and high temperature with a wafer holder (48) containing a wafer (42) of solid sample. A sensor rod (56) moves in response to expansion or contraction of the sample wafer (42) and its movement is measured by either an LVDT sensor (66) or a magnetometer (116). Heat is provided via a heater (30) and pressure is controlled via a pressurization inlet (16) or pressurization fluid (68).

20 Claims, 2 Drawing Sheets

HIGH PRESSURE HIGH TEMPERATURE LINEAR SWELL METER

BACKGROUND

1. Field of Invention

The present invention relates to apparatuses and methods for monitoring, measuring, or analyzing the volumetric expansion or contraction ("swell") of a solid sample.

2. Description of Prior Art

Borehole instability in clay-rich rocks such as shaly sandstones, mudstones and shales is regarded as the prime technical problem area in oil and gas well drilling, and is one of the principal causes of trouble during the drilling process. It has been noted that shales make up over 75% of drilled formations and cause over 90% of wellbore stability problems, many of which result in stuck pipe. Thus, there is a great need for methods and apparatuses to accurately and quantitatively measure the hydration and swelling behavior of shales when exposed to different drilling fluids. Understanding and controlling these behaviors can be vital to the stability of the wellbore.

U.S. Pat. No. 6,247,358 describes a mechanism for the evaluation of shale reactivity. The mechanism requires a sample collection method that is inflexible, difficult to perform, requires a specific hardware mechanism and operation method for sample collection and storage, and is highly specific to only one type of shale testing. These problems prevent the design outlined in the patent from being reliably used to test samples collected under any conditions other than those specified therein.

U.S. Pat. No. 6,247,358 and U.S. Pat. No. 5,275,063 both describe a testing method in which a shale sample is confined within a pressure chamber and exposed to testing fluid under conditions of temperature and constant triaxial pressure. As the sample expands or contracts, pressure is applied to counter the change, preventing the sample from actually expanding or contracting. This methodology addresses only one specific instance of shale reactivity, in which the sample is collected from a core taken from a wellbore. It requires testing apparatus which is complex and expensive to configure, operate and maintain. Thus there is a need for a testing mechanism which can test sample reactivity using a simpler, more flexible and robust mechanism, and without a need for a specific configuration, origin, or substance of sample.

It is an object of this invention to provide a means for measuring the hydration and/or swelling behavior of solid sample material under varying and controllable conditions of temperature and pressure.

It is a further object of this invention to provide a means for testing said solid sample material while either eliminating the need for pressurization fluid, or keeping the exposure of sample material to pressurization fluid to a minimum.

It is a further object of this invention to provide a means for automatically and digitally tracking and recording changes in sample swelling.

It is another object of this invention to provide a specific swelling measurement device which requires substantially less maintenance work than other designs yet meets industry standards of accuracy, reliability, durability, dependability, and ease of cleaning.

SUMMARY OF THE PRESENT INVENTION

A linear swell meter in accord with the present invention comprises a pressure vessel, within which is suspended a wafer holder containing a wafer of sample material and a rod which rests upon the sample wafer and extends up into a sensor apparatus attached to the pressure vessel cap so that as the wafer swells (expands or contracts) the swelling of the sample wafer can be measured. The pressure vessel is filled with a liquid sample. Pressure is supplied to the pressure vessel by means of a pressure port, and heat can be applied to the pressure vessel by means of a heater.

DRAWING FIGURES

Other objects, features and advantages will be apparent from the following detailed descriptions of preferred embodiments taken in conjunction with accompanying drawings in which.

Figure 1:
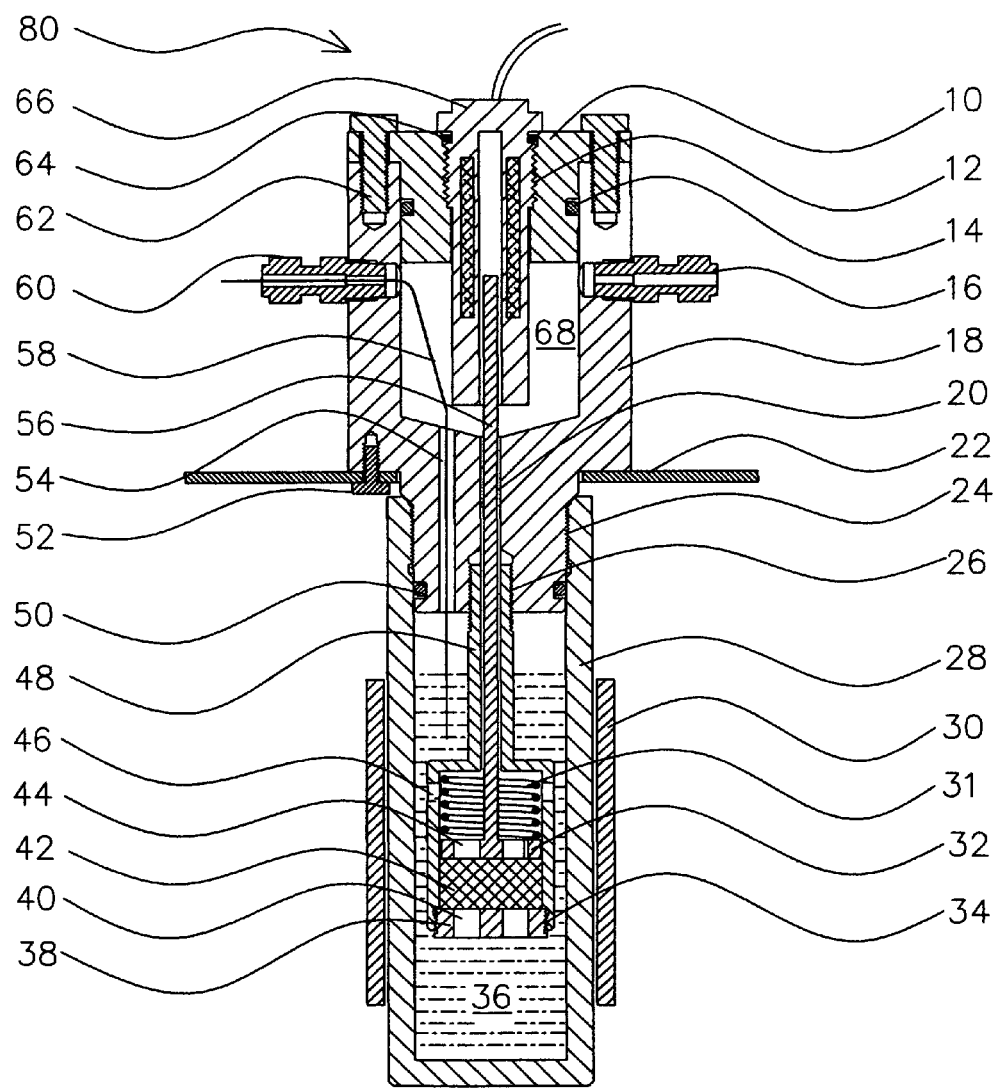
FIG. 1 is a cross-section view of cell assembly 80 in the preferred embodiment of the invention, utilizing an LVDT sensor.

| Reference Numerals in Drawings | | | |
|---|---|---|---|
| 10 | cell cap | 12 | thread |
| 14 | o-ring | 16 | pressure port |
| 16A | pressure port | 18 | cell body |
| 20 | gap | 20A | gap |
| 22 | plate | 24 | thread |
| 26 | thread | 26A | thread |
| 28 | sample cup | 28A | cell body |
| 30 | heater | 30A | heater |
| 31 | spring | 31A | spring |
| 32 | top plate | 32A | top plate |
| 34 | thread | 34A | thread |
| 36 | liquid sample | 36A | liquid sample |
| 38 | bottom plate | 38A | bottom plate |
| 40 | hole | 40A | hole |
| 42 | wafer | 42A | wafer |
| 44 | hole | 44A | hole |
| 46 | hole | 46A | hole |
| 48 | wafer holder | 48A | wafer holder |
| 50 | o-ring | 50A | o-ring |
| 52 | screw | 54 | hole |
| 54A | hole | 56 | rod |
| 56A | rod | 58 | thermal couple |
| 58A | thermal couple | 60 | thermal couple port |
| 62 | screw | 64 | o-ring |
| 66 | LVDT sensor | 68 | chamber |
| 68A | pressurization fluid | 72A | top magnet |
| 74A | set screw | 76A | magnet holder |
| 78A | adaptor | 80 | cell assembly |
| 80A | cell assembly | 82A | thread |
| 83A | conical surface | 84A | o-ring |
| 86A | driving magnet | 88A | stirring magnet |
| 90A | conical surface | 92A | straight bore |
| 94A | magnet mount | 96A | bearing |
| 98A | bearing | 100A | thread |
| 102A | lock nut | 104A | cell bottom |
| 106A | bushing | 108A | pivot |
| 110A | thread | 112A | outlet |
| 114A | cell cap | 116A | magnetometer |

DESCRIPTION

FIG. 1—Embodiment with LVDT Sensor

FIG. 1 is a cross-section view of a cell assembly 80, which consists of a cylindrical cell cap 10 affixed to the top of a cylindrical cell body 18 by means of a screw 62. An o-ring 14 is installed on the outside of cell cap 10 to form a seal with cell body 18. A LVDT sensor 66 is screwed down into the top of cell cap 10 via a thread 12. An o-ring 64 is installed at the top of cell cap 10 to form a seal with LVDT sensor 66. A cylindrical sample cup 28 with closed end bottom is screwed onto the lower end of cell body 18 by means of a thread 24. An o-ring 50 is installed onto the lower end of cell body 18 to form a seal with sample cup 28. Cell assembly 80 is mounted onto a plate 22 and is secured there by means of a screw 52.

A wafer holder 48 is fixed to the lower end of cell body 18 via a thread 26 and extends its lower hollow cylindrical body downward into sample cup 28. A wafer 42 having a disc shape is contained inside of the lower section of wafer holder 48. A top plate 32 rests on top of wafer 42, and a bottom plate 38 supports its bottom. Top plate 32 also connects to the lower end of a rod 56. A spring 31 is positioned around the lower end of rod 56 and above top plate 32. The upper end of rod 56 passes through the center of wafer holder 48 and extends upward into LVDT sensor 66. Bottom plate 38 is attached to the bottom of wafer holder 48 by means of a thread 34.

Sample cup 28 is also filled with a liquid sample 36. A hole 46, located on the side wall of wafer holder 48 and above wafer 42, allows liquid sample 36 to flow through wafer holder 48. The level of liquid sample 36 should at least cover hole 46 to ensure that liquid sample 36 can submerge wafer 42 completely. A hole 44 on top plate 32 and a hole 40 on bottom plate 38 are also provided to ensure good contact between liquid sample 36 and wafer 42.

A thermal couple port 60, set into the upper part of cell body 18, allows the insertion of a thermal couple 58, which extends downward into sample cup 28 through a hole 54. A pressure port 16, also set into the upper part of cell body 18, provides a means by which pressurization media, such as nitrogen or hydraulic oil, can be introduced into cell body 18 and flow into a chamber 68 and then downward through a gap 20 into sample cup 28. A heater 30 is positioned outside sample cup 28 at considerably the same height as wafer 42 and provides temperature control for sample cup 28.

Operation

FIG. 1—Embodiment with LVDT Sensor

In FIG. 1, install o-ring 64 and o-ring 14 onto cell cap 10. Screw LVDT sensor 66 into cell cap 10 via thread 12. Fasten cell cap 10 to cell body 18 via screw 62. Fasten cell body 18 to plate 22 via screw 52.

Attach top plate 32 to rod 56, and drop spring 31 onto rod 56 so that it rests on top plate 32. Insert rod 56 upward into wafer holder 48 so that spring 31 is inside of the hollow cylinder of wafer holder 48. Place wafer 42 into wafer holder 48 and then screw bottom plate 38 onto wafer holder 48 via thread 34. Spring 31 presses top plate 32 downward onto wafer 42 with a preloaded force. The stiffer spring 31 is, the more force is applied to wafer 42. Spring 31 could even be removed, as long as top plate 32 and wafer 42 have good contact. Screw wafer holder 48 into cell body 18 via thread 26.

Fill sample cup 28 with liquid sample 36. Install o-ring 50 onto the lower end of cell body 18 and screw sample cup 28 onto the lower end of cell body 18 via thread 24, immersing wafer 42 into liquid sample 36. Wafer 42 is exposed to liquid sample 36 through hole 46 in wafer holder 48, hole 44 in top plate 32, and hole 40 in bottom plate 38.

During operation, pressure is applied on top of sample 36 by a pressurization media through pressure port 16, chamber 68, hole 54 and gap 20. Heater 30 increases the temperature of sample cup 28. Sample 36 temperature is measured by thermal couple 58. Expansion or contraction of wafer 42 causes top plate 32 to rise or fall. Rod 56, connected to top plate 32, rises or falls within LVDT sensor 66, registering a change in wafer height. This height is transferred to relative swell of wafer 42.

DESCRIPTION

Figure 2:
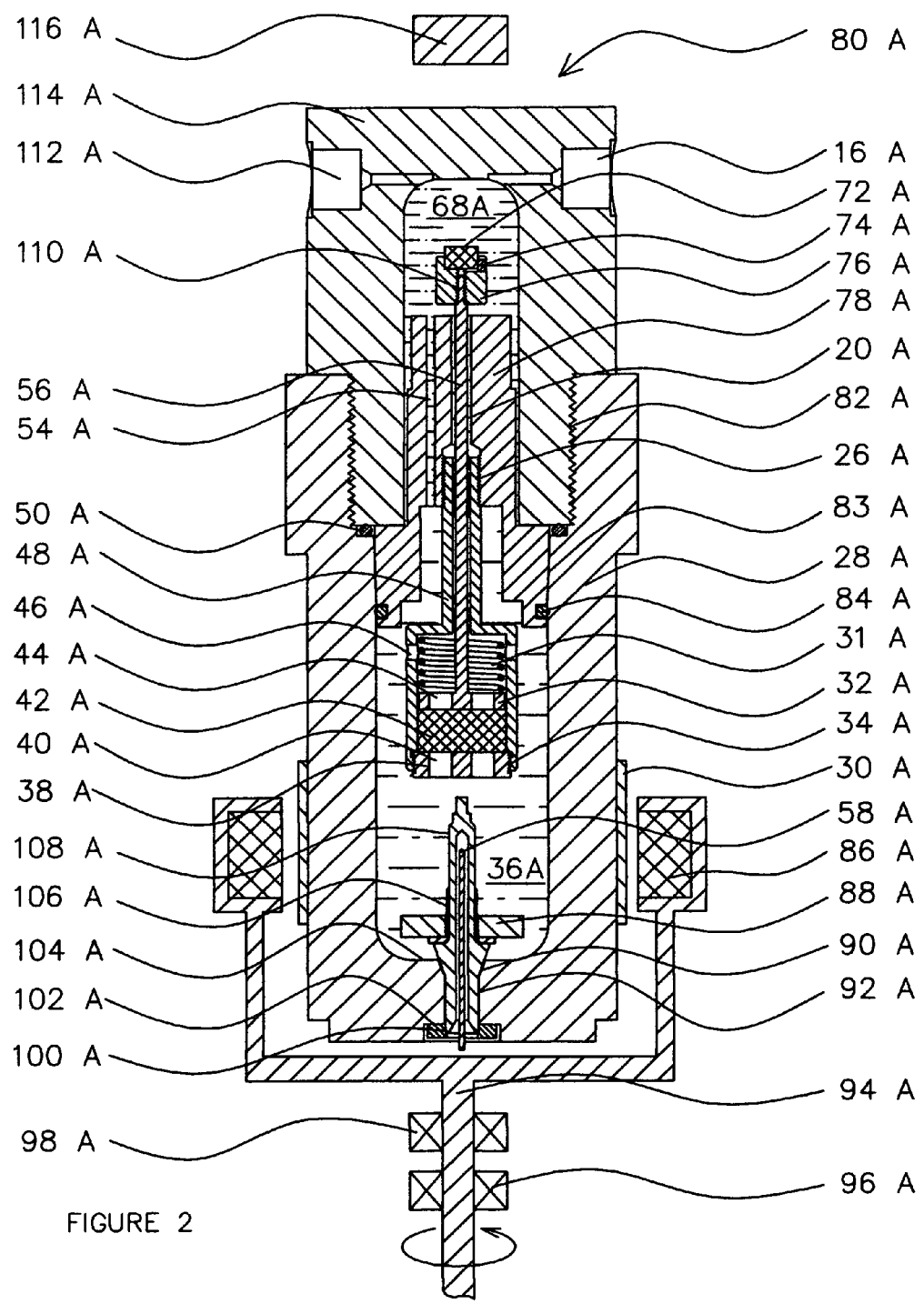
FIG. 2 is an alternative configuration of cell assembly 80A with a different pressure vessel configuration and utilizing a magnetometer.

FIG. 2—Embodiment with Magnetometer Sensor

FIG. 2 is a cross-section view of a cell assembly 80A, which is comprised of a cylindrical cell body 28A and a cylindrical cell cap 114A. Cell cap 114A is screwed onto the upper part of cell body 28A via a thread 82A. An o-ring 50A is installed inside the upper part of cell body 28A and forms a seal with cell cap 114A.

Cell body 28A extends downward to a cell bottom 104A, where a tapered hole with a conical surface 90A and a straight bore 92A is located in the center of cell bottom 104A. A pivot 108A, which is secured to cell bottom 104A by a lock nut 102A through a thread 100A, is seated into said tapered hole through straight bore 92A. Lock nut 102A is tightened to provide initial seal on conical surface 90A between cell bottom 104A and pivot 108A. A thermal couple 58A is inserted into the center of pivot 108A. Radially outward of the outer surface of pivot 108A is a bushing 106A.

Bushing 106A is made of Rulon, Teflon or an equivalent plastic. Radially outward of bushing 106A is a stirring magnet 88A, which can rotate freely on the same central axis of pivot 108A. A pressure port 16A and an outlet 112A set into the upper part of cell cap 114A provide ports for supplying and releasing a pressurization fluid 68A. A magnetometer 116A is located above cell cap 114A.

A magnet mount 94A is rotationally supported on the outside of cell body 28A by a bearing 96A and a bearing 98A. Magnet mount 94A can be rotated by any conventional means such as gear box or motor. A pair of driving magnet 86A is mounted on magnet mount 94A at considerably the same level where stirring magnet 88A is mounted inside of cell body 28A. Heat is provided by a heater 30A.

An adaptor 78A is positioned inside cell body 28A, resting on a conical surface 83A. An o-ring 84A is installed onto adaptor 78A, forming a seal with conical surface 83A.

A wafer holder 48A is fixed to the lower end of adaptor 78A via a thread 26A and extends its lower hollow cylindrical body downward into cell body 28A. A wafer 42A having a disc shape is contained inside of the lower section of wafer holder 48A. A top plate 32A rests on top of wafer 42A, and a bottom plate 38A supports its bottom. Top plate 32A also connects to the lower end of a rod 56A. A spring 31A is positioned around the lower end of rod 56A and above top plate 32A. The upper end of rod 56A passes through the center of wafer holder 48A and extends upward through adaptor 78A. Bottom plate 38A is attached to the bottom of wafer holder 48A by means of a thread 34A. Thus assembled, spring 31A presses top plate 32A downward onto wafer 42A. Rod 56A extends up through wafer holder 48A and adaptor 78A. A magnet holder 76A is attached to the top of rod 56A via a thread 110A. A top magnet 72A is attached to magnet holder 76A via a set screw 74A.

Cell body 28A is mostly filled with a liquid sample 36A, immersing pivot 108A and filling the bottom of adaptor 78A. A hole 46A, located on the side wall of wafer holder 48A and above wafer 42A, allows liquid sample 36A to flow through wafer holder 48A. The level of liquid sample 36A should at least cover hole 46A to ensure that liquid sample 36A can submerge wafer 42A completely. A hole 44A on top plate 32A and a hole 40A on bottom plate 38A are also provided to ensure good contact between liquid sample 36A and wafer 42A.

During operation, pressurization fluid 68A is introduced from pressure port 16A and immerses the top of adaptor 78A. Pressurization fluid 68A is able to flow downward into cell body 28A only via a hole 54A and a gap 20A.

Operation

FIG. 2—Embodiment with Magnetometer Sensor

In FIG. 2, place pivot 108A inside of cell body 28A so that straight bore 92A and conical surface 90A are secured to cell bottom 104A via thread 100A and lock nut 102A. Pivot 108A can be cleaned together with cell body 28A. Fit bushing 106A over pivot 108A. Fit stirring magnet 88A onto pivot 108A on top of bushing 106A. Due to the magnetic coupling between driving magnet 86A and stirring magnet 88A, stirring magnet 88A is able to rotate at the same revolving speed as magnet mount 94A does.

Attach top plate 32A to rod 56A. Drop spring 31A onto rod 56A so that it rests on top plate 32A. Insert rod 56A, spring 31A and top plate 32A into wafer holder 48A. Place wafer 42A into wafer holder 48A, and then screw bottom plate 38A onto wafer holder 48A via thread 34A. Spring 31A presses top plate 32A downward onto wafer 42A with a preloaded force. The stiffer spring 31A is, the more force is applied to wafer 42A. Spring 31A could even be removed, as long as top plate 32A and wafer 42A have good contact. Screw wafer holder 48A into adaptor 78A via thread 26A. Attach magnet holder 76A to the top of rod 56A via thread 110A. Install o-ring 84A onto adaptor 78A. Install top magnet 72A to the top of magnet holder 76A and secure it with set screw 74A.

Fill cell body 28A with liquid sample 36A. Place adaptor 78A into cell body 28A so that o-ring 84A forms a seal with conical surface 83A. Wafer 42A is exposed to liquid sample 36A though hole 46A in wafer holder 48A, hole 44A in top plate 32A, and hole 40A in bottom plate 38A. Drop o-ring 50A into cell body 28A so that it can form a seal with cell cap 114A, and then screw cell cap 114A onto cell body 28A via thread 82A, forming cell assembly 80A.

During operation, pressurization fluid 68A is introduced into cell assembly 80A by means of pressure port 16A or drained from cell assembly 80A by means of outlet 112A, both set into the upper part of cell cap 114A. Pressurization fluid 68A compresses liquid sample 36A with minimal contamination by flowing downward through hole 54A and gap 20A, confining contact between pressurization fluid 68A and liquid sample 36A to the interior of adaptor 78A. Magnet mount 94A rotates on bearing 96A and bearing 98A, causing stirring magnet 88A to rotate as well. Heater 30A increases the temperature which is measured by thermal couple 58A. Expansion or contraction of wafer 42A causes top plate 32A to rise or fall. Rod 56A, connected to top plate 32A, rises or falls. As rod 56A rises or falls, the distance from top magnet 72A to magnetometer 116A changes, registering a change in wafer height. This height is transferred to relative swell of wafer 42A.

Ramifications

In FIG. 1, spring 31 can be removed if it is not necessary to apply a predetermined force on wafer 42.

In FIG. 1, LVDT sensor can be replaced with a high-pressure capacity sensor, ultrasonic sensor, conductivity sensor, eddy current sensor, or any other type of sensor to sense the movement of rod 56 or top plate 32.

In FIG. 2, magnetometer 116A can be replaced with an ultrasonic sensor to sense the movement of magnet holder 76A. This said ultrasonic sensor could locate inside or outside of cell cap 114A.

In FIG. 1, LVDT sensor could be mounted outside of cell assembly 80 while sensing the movement of rod 56 through the cell assembly 80 wall.

In FIG. 1, heater 30 can be a band heater, heating oil bath, heat oven, or radiation heater.

In FIG. 1, sample cup 28 and cell body 18 could be one integrated piece. In this case, liquid sample 36 is introduced to submerge wafer 42 in a way, then pressure is applied on liquid sample 36.

In FIG. 1, wafer holder 48 could be integrated with cell body 18 instead of detachable.

In FIG. 1, hole 40 could be eliminated. This would allow only the top side of wafer 42 to be exposed to liquid sample 36 and move freely.

In FIG. 1, hole 44 could be eliminated. In this case, only the bottom side of wafer 42 is exposed to liquid sample 36, while only the top side of wafer 42 can move freely.

In FIG. 1, hole 44 and hole 40 can be replaced with porous materials as long as a means for allowing liquid sample 36 to contact wafer 42 is provided.

In FIG. 1, wafer 42 can have a cubic shape as long as one face of wafer 42 is allowed to swell freely and at least one face of wafer 42 is in contact with liquid sample 36.

In FIG. 1, wafer 42 can be shaped as a frustum, shaped conically, shaped frustro-conically or shaped as other symmetric shapes. In these cases, wafer 42 circumferential surface is confined and at least one surface mostly perpendicular to wafer 42 axis is exposed to liquid sample 36 and one surface is allowed to move freely.

Conclusion, and Scope

Accordingly, the reader skilled in the art will see that this invention can be used to construct a pivotal high pressure vessel in which a solid sample can be tested for reactivity to a variety of fluids under varying and controllable conditions of pressure and temperature. In so doing, it satisfies an eminent drilling industry need.

Objects and Advantages

From the description above, a number of advantages of my swell meter become evident:

(a) Due to limited number of components, current invention is easy to operate and maintain.

(b) Due to flexibility of design, current invention can be embodied as a stand-alone unit or as an add-on module for an existing high-pressure, high-temperature testing device.

(c) The pressure rating of current invention will only be limited to the pressure rating of its pressure vessel, tubing and valves, which can be up to 60,000 psi.

(d) In one embodiment, the current invention can test solids dynamically and statically under high pressure and high temperature.

Further objects and advantages of my invention will become apparent from a consideration of the drawings and ensuing description.

What I claimed:

1. A solid swell measurement device comprising:
   (a) a substantially vertically positioned sample cell which is detachable from a mating component and is at least partially filled with a liquid sample;
   (b) a solid sample;
   (c) a rigid container holding said solid sample, whereas said rigid container allows at least a swell face of said solid sample to move freely while prohibiting the movement of the remaining surface of said solid sample;
   (d) a liquid contact face of said solid sample is in contact with said liquid sample;
   (e) a pressure port through which pressure can be applied on top of said liquid sample;
   (f) and a means to measure the movement of said swell face of said solid sample.

2. The swell measurement device of claim 1 wherein said means to measure the movement of said swell face of said solid sample is a linear variable differential transformer sensor.

3. The swell measurement device of claim 1 wherein said means to measure the movement of said swell face of said solid sample is a magnetometer.

4. The swell measurement device of claim 1 wherein said means to measure the movement of said swell face of said solid sample is an ultrasonic sensor.

5. The swell measurement device of claim 1 wherein said solid sample has a cylindrical shape.

6. The swell measurement device of claim 1 wherein said swell face of said solid sample is preloaded with a force.

7. The swell measurement device of claim 1 wherein said means to measure the movement of said free moving surface of said solid sample is a non-contact type sensor located outside of said sample cell.

8. The swell measurement device of claim 1 further comprising a means for controlling the pressure of said sample cell.

9. The swell measurement device of claim 1 further comprising a heater to control the temperature of said sample cell.

10. The swell measurement device of claim 1 further comprising a stirrer to provide agitation to said liquid sample.

11. A solid swell measurement device comprising:
    (a) a substantially vertically positioned sample cell which is detachable from a mating component and is at least partially filled with a liquid sample;
    (b) a solid sample with at least a circumferential surface and at least a free moving surface mostly perpendicular to said circumferential surface;
    (c) a rigid container rigidly holding said circumferential surface while allowing said free moving surface to move freely and allowing a sample contacting surface of said solid sample to contact said liquid sample;
    (d) a pressure port through which pressure can be applied on top of said liquid sample;
    (e) and a means to measure the movement of said free moving surface of said solid sample.

12. The swell measurement device of claim 11 wherein said means to measure the movement of said free moving surface of said solid sample is a linear variable differential transformer sensor.

13. The swell measurement device of claim 11 wherein said means to measure the movement of said free moving surface of said solid sample is a magnetometer.

14. The swell measurement device of claim 11 wherein said means to measure the movement of said free moving surface of said solid sample is an ultrasonic sensor.

15. The swell measurement device of claim 11 wherein said free moving surface of said solid sample is preloaded with a force.

16. The swell measurement device of claim 11 wherein said means to measure the movement of said free moving surface of said solid sample is a non-contact type sensor located outside of said sample cell.

17. The swell measurement device of claim 11 further consists of a means for controlling the pressure of said sample cell.

18. The swell measurement device of claim 11 further comprising a heater to control the temperature of said sample cell.

19. The swell measurement device of claim 11 further comprising a stirrer to provide agitation to said liquid sample.

20. A solid swell measurement device comprising:
    (a) a substantially vertically positioned sample cell which is detachable from a mating component and is at least partially filled with a liquid sample;
    (b) a solid sample;
    (c) a rigid container holding said solid sample, whereas said rigid container allows at least a swell face of said solid sample to move freely while prohibiting the movement of the remaining surface of said solid sample;
    (d) a liquid contact face of said solid sample is in contact with said liquid sample;
    (e) a means to measure the movement of said swell face of said solid sample;
    (f) a pressurization fluid applied to the top of said liquid sample, introduced into said sample cell through a pressure port;
    (g) and a means to control the pressure of said liquid sample.

* * * * *